US00PP36088P2

(12) United States Plant Patent
Grosser

(10) Patent No.: US PP36,088 P2
(45) Date of Patent: Sep. 3, 2024

(54) ***CITRUS* PLANT NAMED '18A-9-39'**

(50) Latin Name: ***Citrus* sp.**
Varietal Denomination: 18A-9-39

(71) Applicant: Florida Foundation Seed Producers, Inc., Marianna, FL (US)

(72) Inventor: Jude Grosser, Winter Haven, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 18/369,731

(22) Filed: Sep. 18, 2023

(51) Int. Cl.
*A01H 5/08* (2018.01)
*A01H 6/78* (2018.01)

(52) U.S. Cl.
USPC ..... Plt./201
CPC ..... *A01H 6/785* (2018.05)

(58) Field of Classification Search
USPC ..... Plt./201, 202
CPC ..... A01H 5/0806
See application file for complete search history.

(56) References Cited

U.S. PATENT DOCUMENTS

| | | | |
|---|---|---|---|
| PP10,480 | P | 7/1998 | Nadori |
| PP17,863 | P3 | 7/2007 | Roose et al. |
| PP21,356 | P3 | 10/2010 | Gmitter, Jr. et al. |
| PP28,091 | P3 | 6/2017 | Grosser |

OTHER PUBLICATIONS https://citrusindustry.net/2022/09/14/scion-selections-highlighted-at-expo/; Sep. 14, 2022; 3 pages.*
https://www.fdacs.gov/content/download/62638/file/2018-annual_report_combined.pdf; 2018; 20 pages.*
https://citrusindustry.net/2021/10/27/gator-bites-competition-for-clementines/; Oct. 27, 2021; 2 pages.*
In re Wingen; Feb. 2, 2023; 9 pages.*

* cited by examiner

*Primary Examiner* — Kent L Bell
(74) *Attorney, Agent, or Firm* — Koenig IP Works, PLLC; Katherine Koenig

(57) ABSTRACT

A new and distinct cultivar of citrus plant named '18A-9-39', characterized by an easy-to-peel, nearly seedless, tangerine-type fruit with a very rich, sweet, and pleasant flavor; high sugar content in the fruit; vibrant orange fruit color; and good tolerance to HLB, especially when trees are supplemented with controlled release fertilizer (CRF) containing an enhanced micronutrient package.

11 Drawing Sheets

Genus and species: *Citrus* sp.
Cultivar denomination: '18A-9-39'.

CROSS-REFERENCE TO RELATED APPLCIATIONS

N/A.

ACKNOWLEDGEMENT OF FEDERAL RESEARCH SUPPORT

N/A.

BACKGROUND OF THE NEW CULTIVAR

The present invention relates to a new and distinct cultivar of *Citrus* plant, botanically known as *Citrus* sp. and hereinafter referred to by the name '18A-9-39'.

The new *Citrus* cultivar '18A-9-39' is a triploid hybrid from an interploid cross, made in Gainesville, Florida, of a diploid monoembryonic 'Clementine' mandarin (*Citrus clementina* or *Citrus reticulata*) (female parent; not patented) crossed with an allotetrapliod somatic hybrid (protoplast fusion) of ['LB8-9' (U.S. Plant Pat. No. 21,356, commercially available as Sugar Belle) 'Clementine' mandarin, *Citrus clementina* or *Citrus reticulata* (not patented) x 'Minneola' tangelo ('Duncan' grapefruit, *Citrus paradisi* x 'Dancy' tangerine (*Citrus reticulata*) (not patented)]+['Murcott' tangor (*Citrus reticulata* Blanco x *Citrus sinensis* L. Osbeck)] (unnamed pollen parent; not patented); obtained via embryo rescue. The original tree was planted in a growing facility in Gainesville, Florida, and was grafted to 'Swingle' citrumelo rootstock in June of 2010. True-to-typeness through asexual propagation was demonstrated by three additional trees grafted to 'UFR-17' (U.S. Plant Pat. No. 28,091) rootstock and planted in Gainesville, Florida, in Fall of 2016.

Plant Breeder's Rights for this cultivar have not been applied for. The new *Citrus* cultivar '18A-9-39' has not been made publicly available more than one year prior to the filing of this application.

SUMMARY

The new *Citrus* cultivar '18A-9-39' has not been observed under all possible environmental conditions. The phenotype of the new cultivar may vary with variations in environment and cultural practices such as temperature, light intensity, fertilization, irrigation, and application of plant growth regulators without any change in genotype.

The new *Citrus* cultivar '18A-9-39' produces a Clementine-sized, easy-peel, nearly seedless tangerine-type fruit with a very rich, sweet, and pleasant flavor. Fruit matures in early December and holds well through January. Fruit colors well on the tree under Florida conditions (without cold induction), both internally and externally, with bright orange external color becoming more intense in late December and January. Fruit can generally be picked without clipping, as only an occasional fruit plugs. Fruit of '18A-9-39' has a high sugar content and sweet yet rich flavor. This selection has potential to compete in the lucrative easy-to-peel snack citrus market (for example, CUTIES® fruit, Sun Pacific Shippers, L.P. and HALOS® fruit, The Wonderful Company LLC). Existing trees have yielded quite well, especially on 'UFR-17' rootstock. For example, yield data from 3.5-year-old trees on 'C-35' rootstock (not patented) showed the average production per tree was 70.8 kg of fruit with a mean fruit weight of approximately 110 g, which his similar to that of 'Clementine'. Observed cropping on 'UFR-17' has been comparable to that of heavy cropping 'W. Murcott' (not patented) and 'Tango' (U.S. Plant Pat. No. 17,863) mandarin varieties. 'W. Murcott' is not patented, but some authorities believe 'W. Murcott' may be identical to a mandarin cultivar known as 'Afourer' (not patented) and also as 'Nadorcott' (U.S. Plant Pat. No. 10,480). Fruit on trees having 'UFR-17' rootstock is larger and peels easier than the fruit on the original tree. Tolerance to HLB (Huanglongbing or *Citrus* greening disease) has been good, and even better than most mandarin hybrids in the Applicant's breeding program, especially with the trees on 'UFR-17' rootstock that have been grown with supplemental FLORIKAN® CRF (controlled release fertilizer) (Profile Products LLC) that contains an enhanced micronutrient package. Plantings on additional rootstocks are needed to determine optimal performance.

DESCRIPTION OF THE FIGURES

The accompanying photographs (as shown in FIGS. 1-12) illustrate the overall appearance of 4.5-year-old plants of the new *Citrus* cultivar '18A-9-39'. These photographs show the colors as true as can be reasonably obtained in colored reproductions of this type. Colors in the photographs may differ slightly from the color values cited in the detailed botanical description, which accurately describe the colors of the new *Citrus* cultivar. It is noted that all of the photographs shown in the Figures were taken of trees with HLB infections.

DETAILED BOTANICAL DESCRIPTION OF THE CULTIVAR

Figure 1:
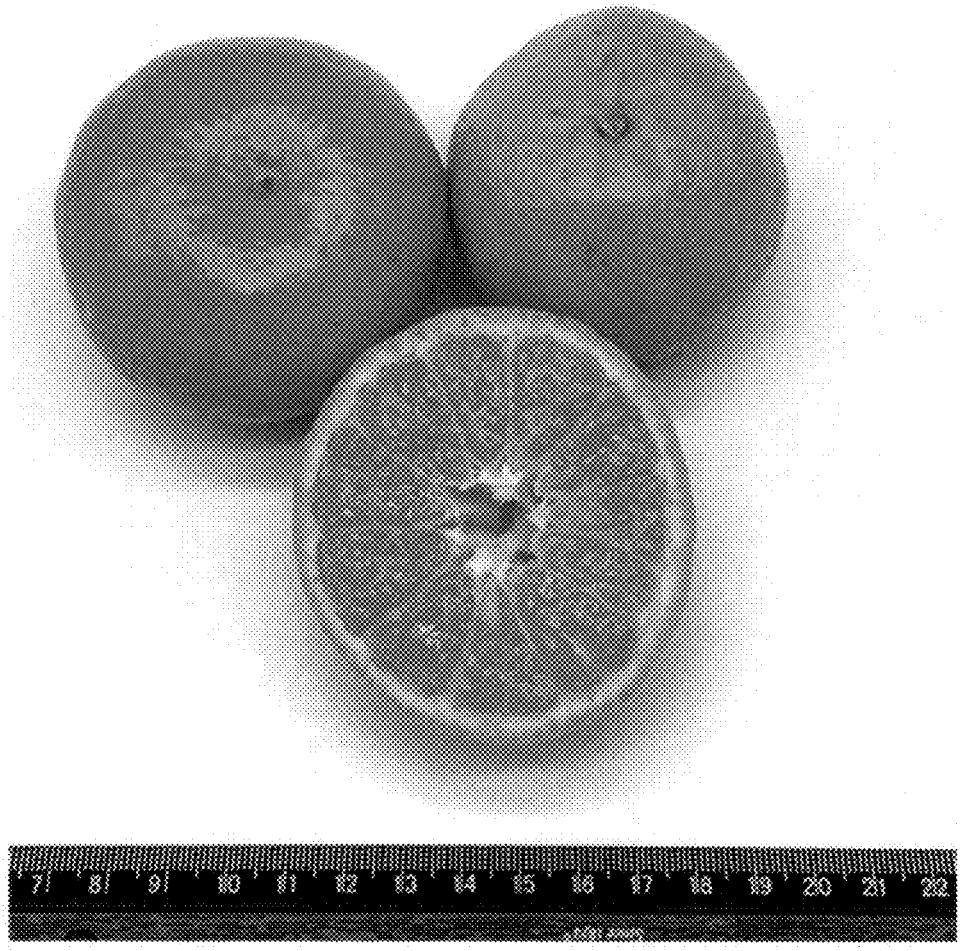
FIG. 1 and FIG. 2 show whole and cut fruit of the new *Citrus* cultivar '18A-9-39' as shown and described herein.
Figure 2:
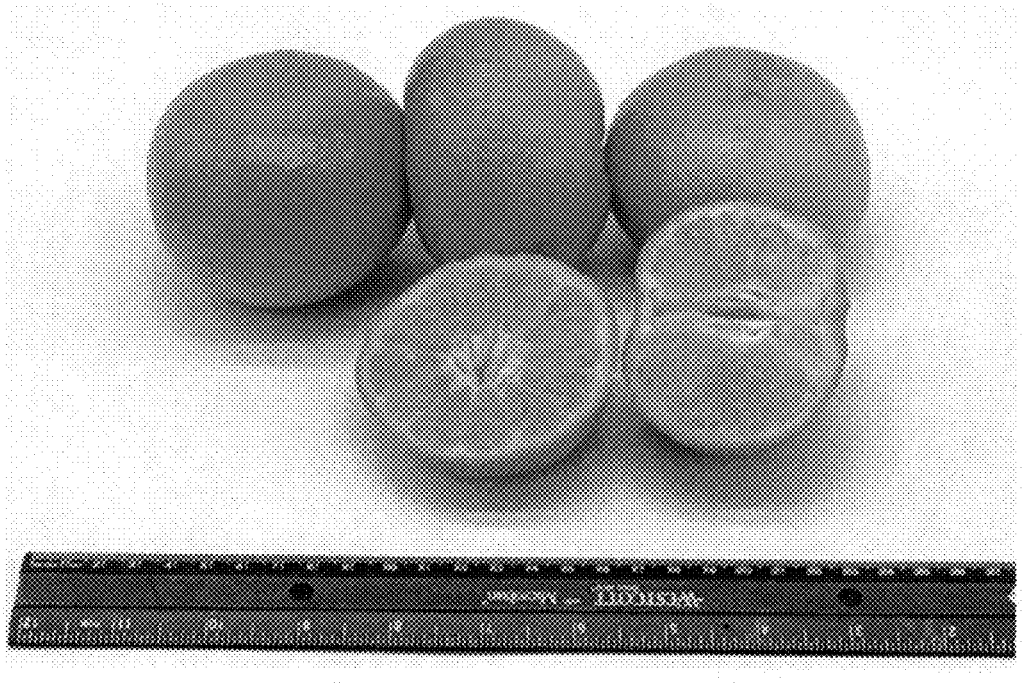
Figure 3:
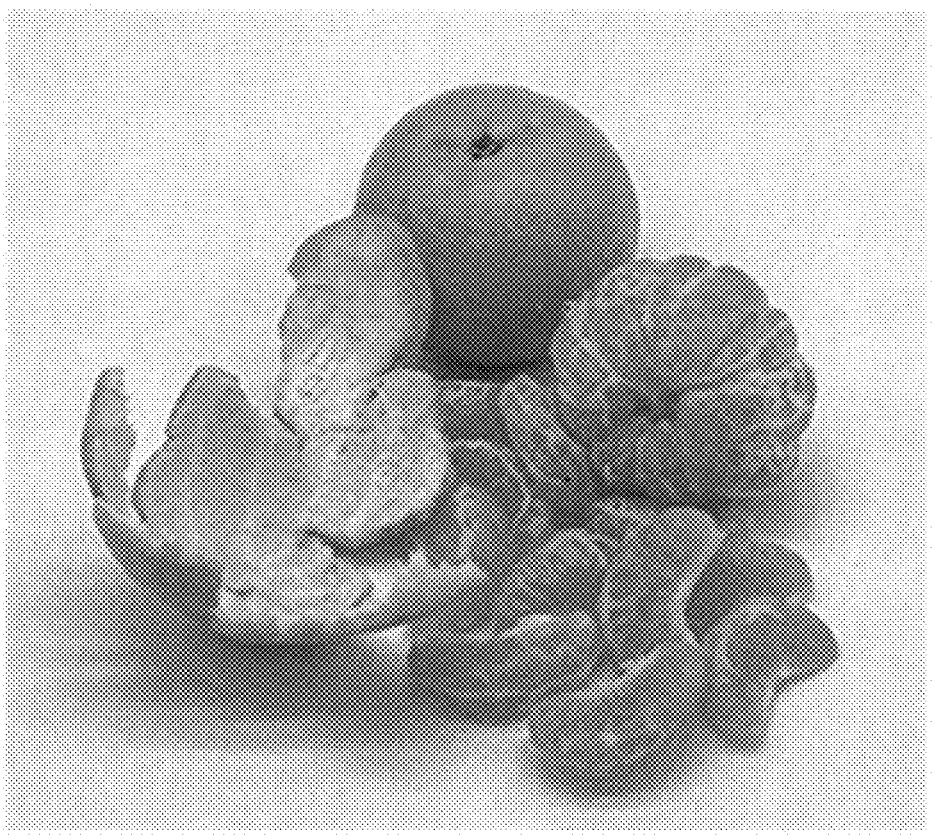
FIG. 3 shows whole and sectioned fruit of the new *Citrus* cultivar.
Figure 4:
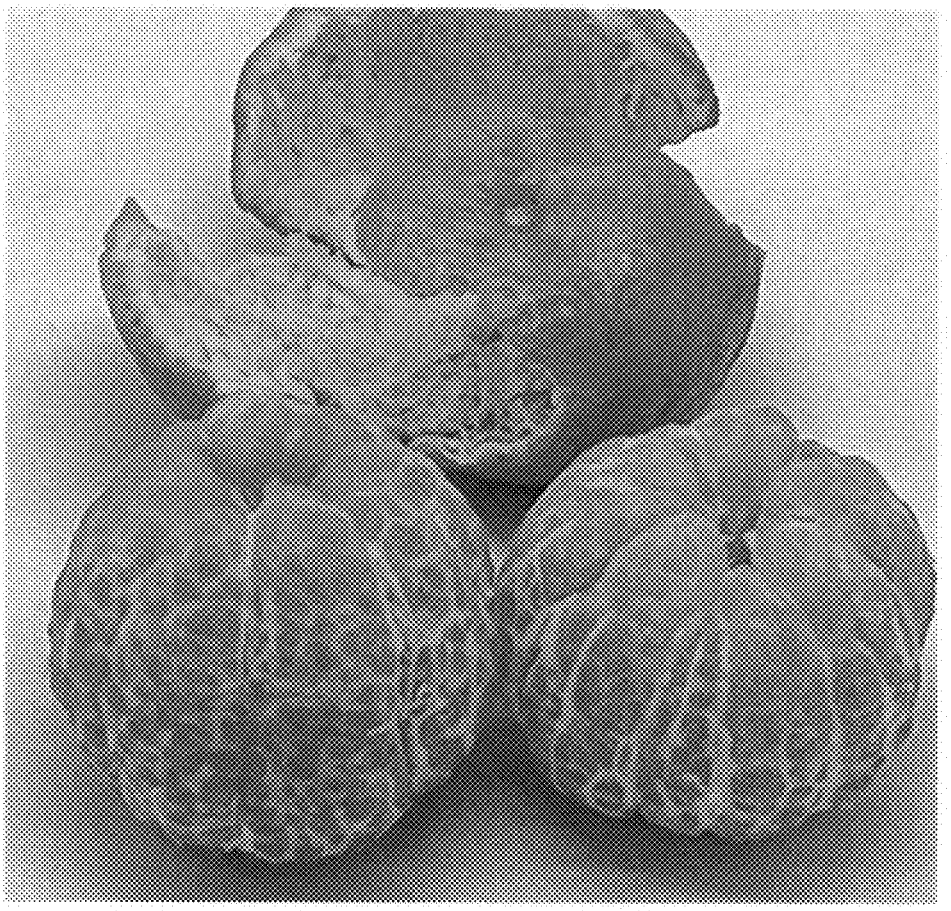
FIG. 4 shows peeled fruit of the new *Citrus* cultivar.
Figure 5:
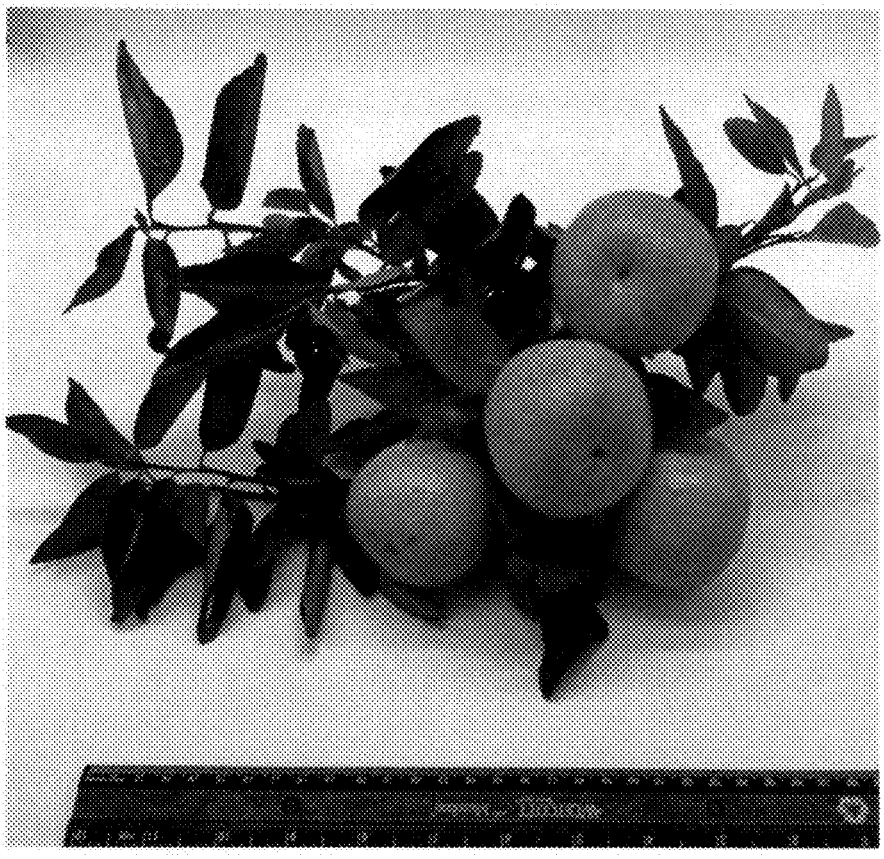
FIG. 5 shows whole fruit and cut foliage of the new *Citrus* cultivar.
Figure 6:
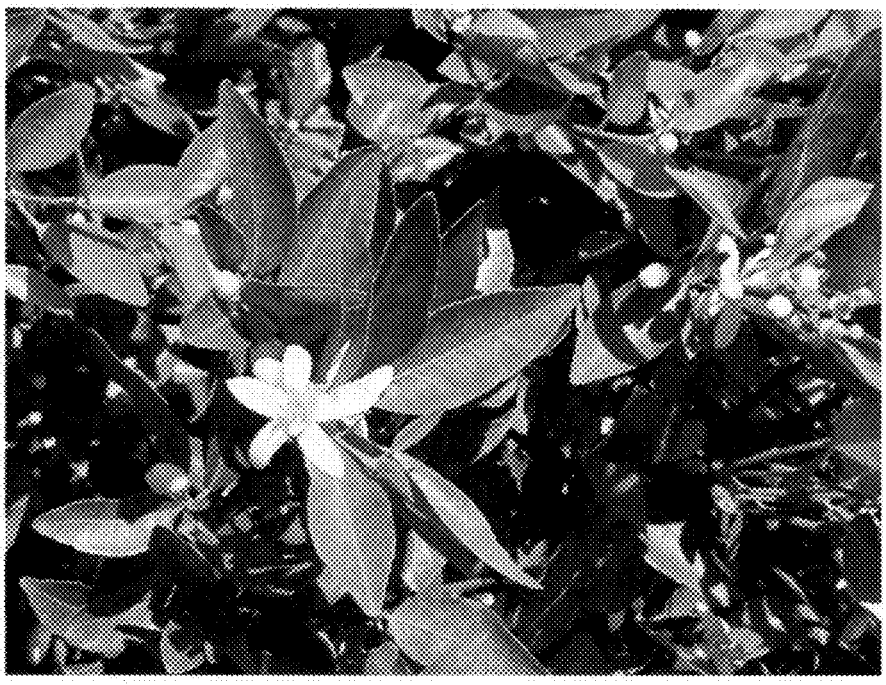
FIG. 6 shows flowers and foliage of the new *Citrus* cultivar.
Figure 7:
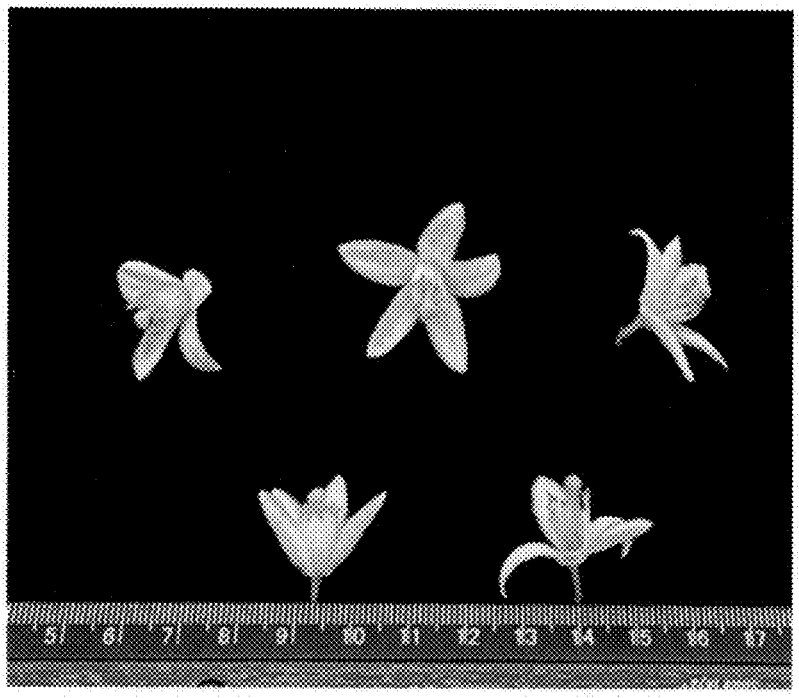
FIG. 7 and FIG. 8 show close-up views of mature flowers of the new *Citrus* cultivar.
Figure 8:
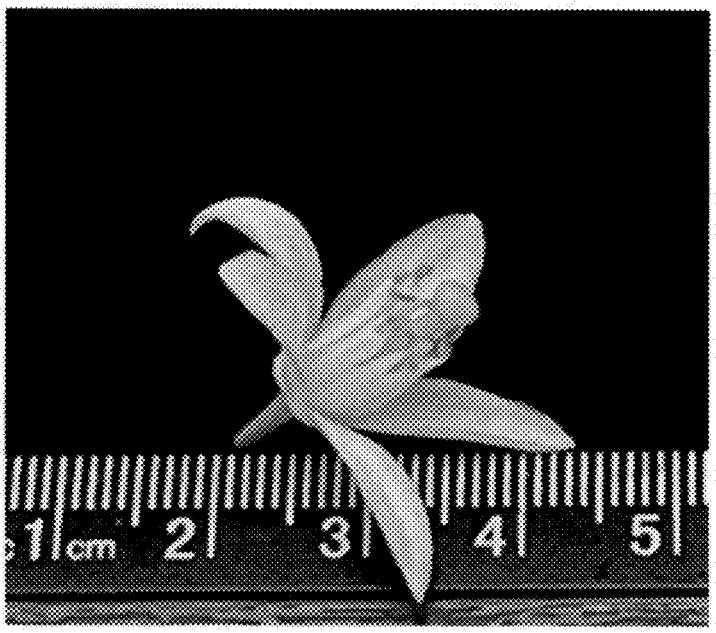
Figure 9:
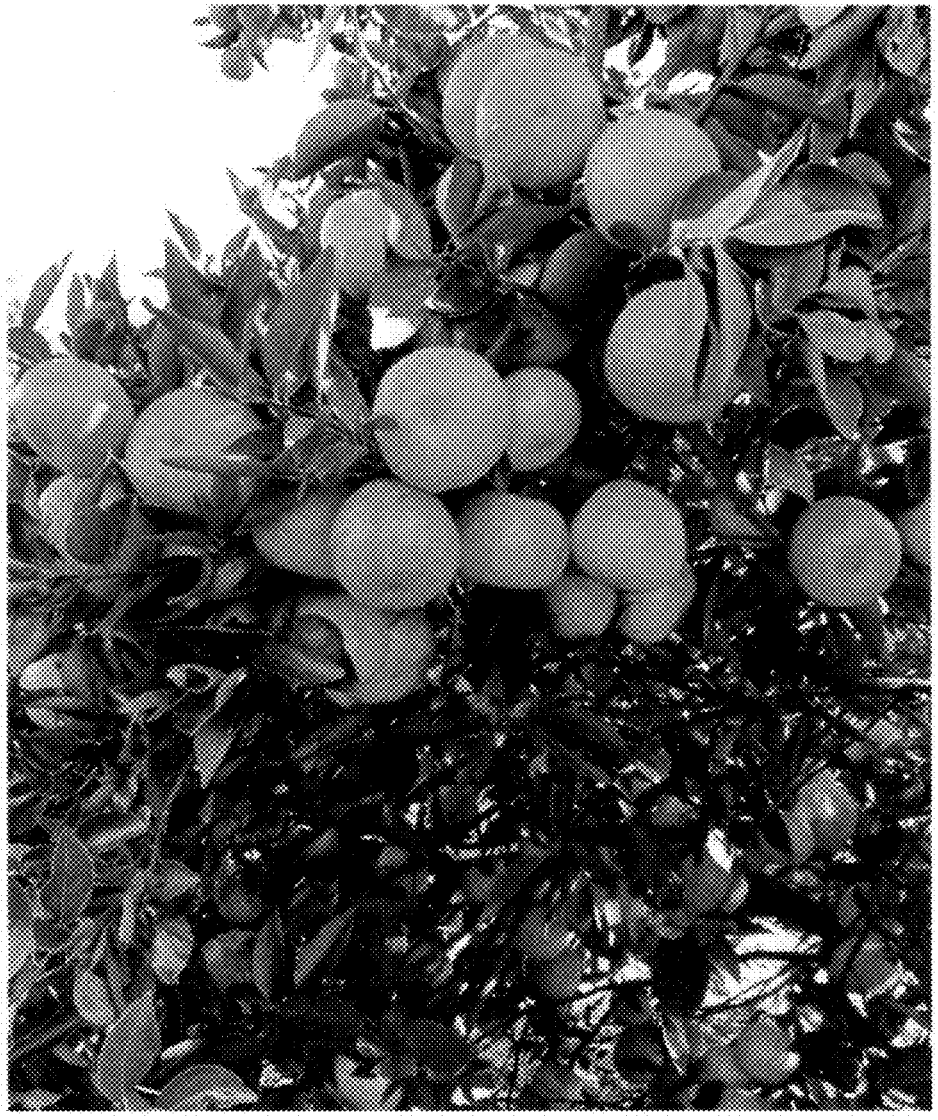
FIG. 9 shows fruit on a branch of the new *Citrus* cultivar.
Figure 10:
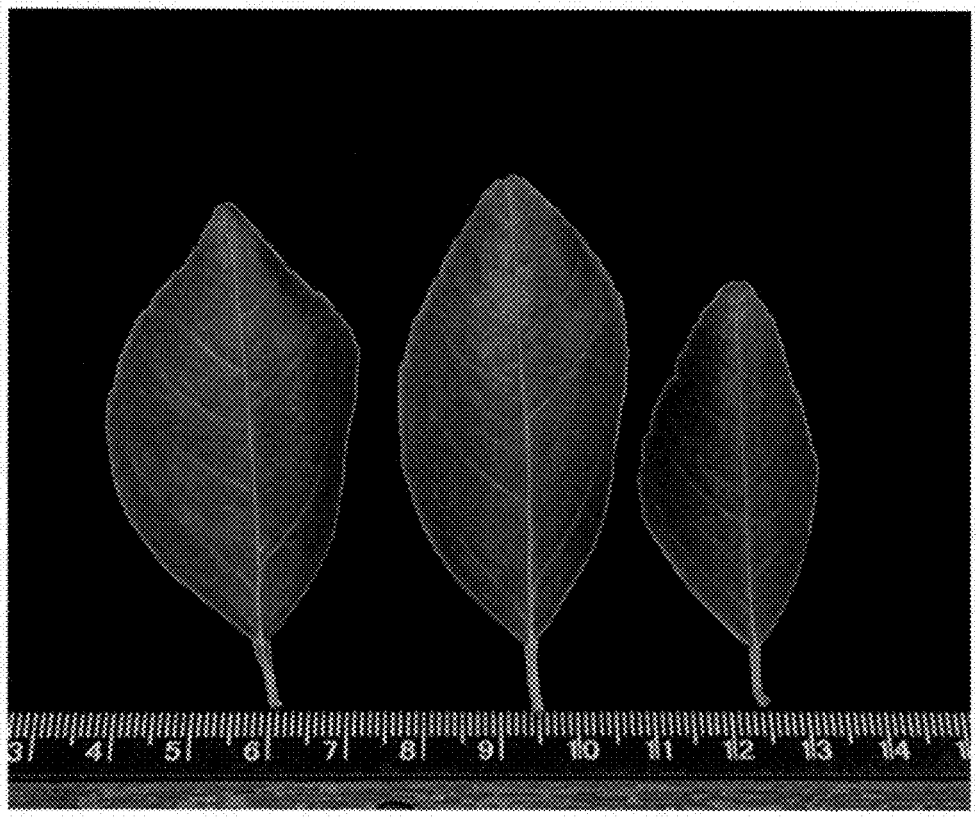
FIG. 10 shows a close-up view of leaves of the new *Citrus* cultivar.
Figure 11:
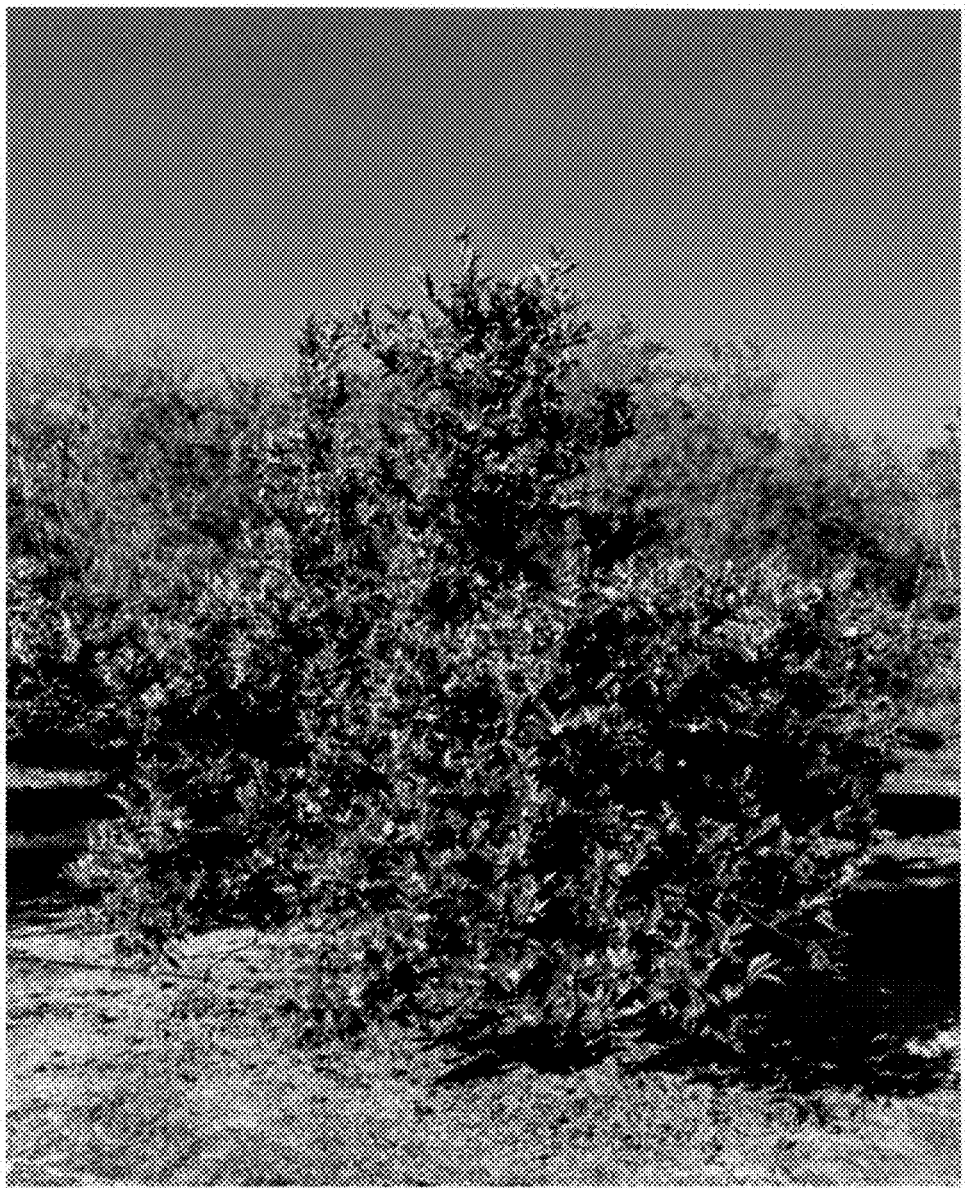
FIG. 11 and FIG. 12 show the overall plant growth habit of the new *Citrus* cultivar.
Figure 12:
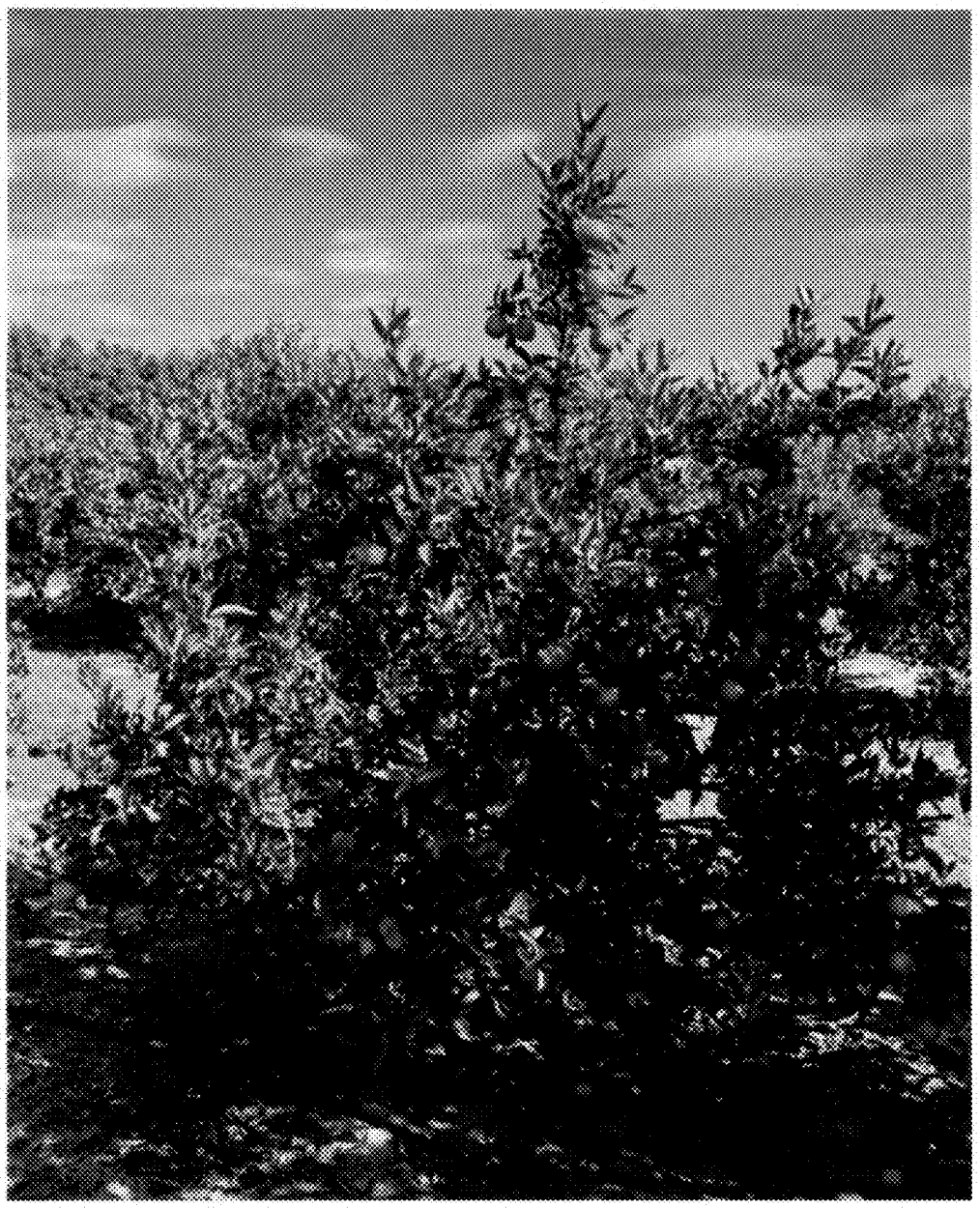

The following detailed description of the new *Citrus* cultivar '18A-9-39' was obtained using a 4-5 year-old tree growing on 'UFR-17' rootstock in Lake Alfred, Florida, growing in well-drained sands and soil with poor organic content. The tree was growing under subtropical growing conditions, with hot, humid, and rainy summers (June through August) and mild but variable weather the rest of the year, and generally with a few mild freezes. Leaf and flower data was collected in March, and mature fruit data was collected in November. The colors (except those in common terms) are described from R. H. S. Colour Chart published by The Royal Horticultural Society in London (Second Edition), in association with the Flower Council of Holland.

Botanical Description

Botanical classification:

*Family.*—Rutaceae.

*Botanical name.*—*Citrus* sp.

*Common name.*—Mandarin.

*Cultivar.*—'18A-9-39'.

Parentage: The new *Citrus* cultivar '18A-9-39' is a triploid hybrid from an interploid cross of a diploid monoembryonic 'Clementine' mandarin (*Citrus clementina* or *Citrus reticulata*) (female parent; not patented) crossed with an allotetrapliod somatic hybrid (protoplast fusion) of ['LB8-9' (U.S. Plant Pat. No. 21,356, commercially available as Sugar Belle) ('Clementine' mandarin, *Citrus clementina* or *Citrus reticulata* x 'Minneola' tangelo ('Duncan' grapefruit, *Citrus paradisi* x 'Dancy' tangerine (*Citrus reticulata*)]+['Murcott' tangor (*Citrus reticulata* Blanco x *Citrus sinensis* L. Osbeck) (not patented)] (unnamed pollen parent; not patented).

Propagation: Field trees were propagated using standard *Citrus* nursery techniques. Rootstock liners were grown from nucellar seed, and the scion was grafted onto the rootstock using the standard inverted "T" graft method.

Tree description:

*Ploidy.*—Triploid.

*Size.*—Medium.

*Tree height.*—2.8 meters.

*Tree canopy diameter.*—2.8 meters.

*Vigor.*—Moderate.

*Density.*—Canopies are moderately dense.

*Tree shape* (*form*).—Oblate shape.

*Growth habit* (*current season*).—Both upright and lateral growth.

Trunk:

*Trunk diameter.*—7.5 cm at 30 cm above the ground.

*Trunk texture.*—Relatively smooth.

*Trunk bark color.*—RHS N199 D (Grey-Brown Group).

Branches:

*Branch length.*—2.1 meters on average.

*Branch diameter.*—2.9 cm on average.

*Crotch angle.*—Acute, being 80-85 degrees on average (less than 90 degrees) in the middle of the tree, while some on the outside of the tree are obtuse, being 100-105 degrees on average (more than 90 degrees).

*Branch texture.*—Medium rough.

*Branch color.*—RHS 199 B (Grey-Brown Group).

*Branch spines.*—Newly propagated plants have very small spines on the initial primary stem growing from the grafted bud, and not on any other subsequent branches. The length of each branch spine is less than 10 mm. There is one spine per node on the initial stem, and they disappear over time.

Foliage description:

*Size* (*lamina average*).—Length: 97 mm on average. Width: 45 mm on average. Length to width (L:W) ratio: 2:4 on average.

*Thickness.*—Relatively thick.

*Type.*—Simple (unifoliate).

*Shape.*—Elliptical. Apex: Retuse. Base: Acute.

*Margin.*—Dented with a split end.

*Surface.*—Upper surface: Smooth. Lower surface: Medium venation, with veins being pinnately netted.

*Color.*—Upper (adaxial) surface: RHS N 137B (Green Group). Lower (abaxial) surface: RHS 139C (Green Group).

*Petiole.*—Shape and attachment: Brevipetiolate; shorter than leaf lamina. Shape (petiole wing): Obovate with narrow end at the base. Length: 10 mm on average. Width: 1 mm on average. Color: RHS N 137C (Green Group).

Inflorescence description:

*Flower type.*—Hermaphrodite.

*Flowering bearing.*—Single or cluster. Branches have flowers grown in cluster, and each cluster consists of 3-6 flowers. Individual flowers grow from leaf terminals and leaf axillaries.

*Flower diameter.*—Fully open flower with average diameter of 24 mm.

*Flower depth.*—18 mm on average.

*Flower blooming period.*—Generally March, but depends on weather pattern. First bloom: Late February. Full bloom: March.

*Fragrance.*—Fragrant.

*Flower bud size.*—Length, initial visible flower bud: 1.5 mm on average. Length, mature buds before opening: 20 mm on average. Diameter, initial visible flower bud: 1.3 mm on average. Diameter, mature bud: 5.3 mm on average.

*Flower bud shape.*—Initial visible flower bud with round dome shape; mature flower bud with elongated olive shape.

*Flower bud color* (*RHS*).—Initial visible flower bud: 144B (Yellow Green Group) for the initial visible flower bud. Mature bud: RHS NN 155C (White Group) for mature buds.

*Fertility.*—Appears to be self-fertile.

*Petals.*—Number (per flower): 5. Petal length: 15 mm on average. Petal width: 5.2 mm on average. Petal shape: Flat spatula shape. Apex shape: Smooth with obtuse angle. Base shape: Obtuse. Color: Upper surface: RHS NN 155B (White Group). Lower surface: RHS NN 155A (White Group). Margin: Smooth.

*Sepals.*—Number (per flower): 5. Shape: Delta-shaped with acute angle at the apex; however, some have a flat angle at the apex. Width: 2.5 mm on average. Apex shape: Acute angle at apex; however, some have a flat angle at the apex. Margin: Smooth. Color: Upper surface: RHS 157B (Green White Group). Lower surface: RHS 157C (Green White Group).

*Pedicel.*—Length: 9.5 mm on average. Diameter: 1 mm on average. Color: RHS 144D (Yellow Green Group).

*Stamen.*—Number (per flower): 22 on average. Length: 11.5 mm on average.

*Anther.*—Length: 2 mm on average. Width: 0.8 mm on average. Color: RHS 14A (Yellow Orange Group). Pollen color (general): RHS 13B (Yellow Group). Pollen amount: Abundant.

*Pistil.*—Number (per flower): 1. Length: 10 mm on average. Color: RHS 154B (Yellow Green Group). Style length: 9 mm on average. Style diameter: 1 mm on average. Style color: RHS 144D (Yellow Green Group). Ovary shape: Oval shape. Ovary diameter: 2.5 mm on average. Ovary color: RHS 145B (Yellow Green Group).

Fruit:

*Size.*—Uniform, small to medium in size.

*Average weight* (*per individual fruit*).—140 grams.

*Length* (*height*).—6.0 cm on average.

*Diameter.*—6.7 cm on average.

*Shape.*—Spherical, with the broadest part of the fruit being located slightly below the middle.

*Shape* (*cross section*).—Round.

*Apex.*—Round.

*Base.*—Round.

*Harvest.*—Date of first pick: Early December in Florida. Date of last pick: Late January in Florida.

*Fruit stem.*—Length: 10 mm on average. Diameter: 3 mm on average. Color: RHS 189A (Greyed-Green Group).

*Rind.*—Adherence: Adherence of albedo (mesocarp) to flesh (endocarp) is weak and the rind is easy to peel. Thickness: Thin; 3-4 mm on average. Firmness: Medium firm. Surface texture: Medium smooth. Color: Flavedo (epicarp): RHS N25B (Orange Group). Albedo (mesocarp): RHS 19C (Yellow-Orange Group). Style end: Closed. Rind oil cell density: 100-150 cells/square cm. Oil gland size: Big; 0.9 mm on average.

*Flesh.*—Number of segments: 11 on average. Segment length: 5.5 cm on average. Segment width: 2.5 cm on average.

*Juice.*—Presence: Abundant. Color: RHS 24A (Orange Group). Texture: Soft to medium. Vesicles: Length: 10 mm on average. Diameter (thickness): 3 mm on average. Juice quality: Brix: 13.5-17 (increases as fruit is held on tree). Acidity (average): 0.8%. Ratio: 16.8-21 (increases as fruit is held on tree). Juice color: 39.5 (*Citrus* Index Number). Lb. solid/box: Not available.

*Seeds.*—Number: 0-3 seeds per fruit, with an average of 2 seeds per fruit in trees with cross pollination. Shape: Tear-drop shaped. Length: 8-15 mm. Diameter: 3.7 mm. Color: Outer seed coat: RHS 159C (Orange-White). Inner seed coat: RHS 165B (Greyed-Orange). Embryo and cotyledon: RHS 158B (Yellow-White).

Resistance to disease: Susceptible to HLB (Huanglongbing), but more tolerant than most mandarin varieties known to the Inventor, especially when trees are supplemented with controlled release fertilizer (CRF) containing an enhanced micronutrient package. No other disease issues have been observed, including *Citrus* canker or *Alternaria* spp.

Fruit productivity rating (scale of 1-5 with 1 being very low fruit production and 5 being maximum fruit production, in comparison with other commercial varieties known to the Inventor): '18A-9-39' score is 5.

HLB disease index rating (scale of 1-5 with 1 being very poor health, near death, and 5 being completely healthy, in comparison with other commercial varieties known to the Inventor). The score of '18A-9-39' is 4.

Comparison with Known Cultivars

The new *Citrus* cultivar '18A-9-39' can be distinguished from later season 'W. Murcott' and 'Tango' varieties (for example, those sold commercially as CUTIES® and HALOS®) in that the color of the fruit of the new cultivar '18A-9-39' develops much more robustly under typical Florida conditions than these commercial varieties, and the fruit of '18A-9-39' is also more flavorful. However, fruit from cross-pollinated blocks can contain an average of 2 seeds per fruit, whereas the commercial varieties CUTIES® and HALOS® rarely have seeds due to cultivation practices (for example, 'W. Murcott' trees in California are covered with nets during bloom to prevent cross pollination, and thus seed production in the fruit; otherwise, 'W. Murcott' fruit contains many seeds). Evidence suggests that most of the fruit of '18A-9-39' will be seedless if the trees are grown in a solid block (for example, as the commercial variety Sugar Belle), especially if planted blocks are not immediately adjacent to sweet oranges or grapefruit.

The new *Citrus* cultivar '18A-9-39' can be distinguished from its parental cultivar 'Clementine' in that '18A-9-39' displays later maturity and a more robust flavor. The new *Citrus* cultivar '18A-9-39' can be distinguished from its parental cultivar 'Murcott' in that '18A-9-39' has a more vivid orange external color, whereas 'Murcott' has a poor external color. The new *Citrus* cultivar '18A-9-39' can be distinguished from its parental cultivar 'LB8-9' (Sugar Belle) and somatic hybrids fruit of ['Murcott'+'LB8-9'] in that fruit of '18A-9-39' are smaller than those of 'LB8-9' and somatic hybrids fruit of ['Murcott'+'LB8-9'].

What is claimed is:

1. A new and distinct cultivar of *Citrus* plant named '18A-9-39' as illustrated and described herein.

* * * * *